(12) United States Patent
MacGillivray

(10) Patent No.: US 9,937,177 B2
(45) Date of Patent: Apr. 10, 2018

(54) THERAPEUTIC COMPOUNDS

(71) Applicant: UNIVERSITY OF IOWA RESEARCH FOUNDATION, Iowa City, IA (US)

(72) Inventor: Leonard R. MacGillivray, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 15/482,323

(22) Filed: Apr. 7, 2017

(65) Prior Publication Data

US 2017/0304304 A1 Oct. 26, 2017

Related U.S. Application Data

(60) Provisional application No. 62/320,202, filed on Apr. 8, 2016.

(51) Int. Cl.
| | |
|---|---|
| *A01N 43/54* | (2006.01) |
| *A01N 43/90* | (2006.01) |
| *A61K 31/517* | (2006.01) |
| *A61K 31/519* | (2006.01) |
| *C07D 239/70* | (2006.01) |
| *A61K 31/513* | (2006.01) |
| *C07D 401/14* | (2006.01) |

(52) U.S. Cl.
CPC .......... *A61K 31/513* (2013.01); *A61K 31/517* (2013.01); *C07D 401/14* (2013.01)

(58) Field of Classification Search
CPC ..................................................... A61K 31/517
USPC ....................................................... 514/258.1
See application file for complete search history.

(56) References Cited

PUBLICATIONS

Dudovitz, et al., "Polymorphic Hydrogen-bonding Motifs and Reactivity in Co-crystals of 5-fluorouracil", Presented at The 11th Annual Spring Undergraduate Research Festival, University of Iowa, #30, 2 pages, Apr. 8, 2015.
Duncan, et al., "Quantitative and regiocontrolled corss-photocycloaddition of the anticancer drug 5-fluorouracil achieved in a cocrystal", Chem Commun 52, 13109-13111 (2016).
Jin, et al., "Biocompatible Drug Delivery System for Photo-Triggered Controlled Release of 5-Fluorouracil", Biomacromolecules 12(10), 3684-3691 (2011).

*Primary Examiner* — Jeffrey H Murray
(74) *Attorney, Agent, or Firm* — Viksnins Harris Padys Malen LLP

(57) ABSTRACT

The invention provides a compound of formula I:

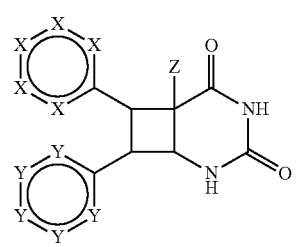

wherein X, Y, Z have any of the values defined in the specification or a salt thereof. The compound is useful as anti-cancer agents. The invention also provides processes and intermediates disclosed herein that are useful for preparing a compound of formula I or a salt thereof.

13 Claims, 7 Drawing Sheets

Olefin separations:
3.44 Å, 3.57 Å

THERAPEUTIC COMPOUNDS

CROSS-REFERENCE TO RELATED APPLICATIONS

This application claims priority to U.S. Provisional Application No. 62/320,202, filed Apr. 8, 2016. The entire content of the application referenced above is hereby incorporated by reference herein.

GOVERNMENT FUNDING

This invention was made with government support under DMR-1408834 awarded by the National Science Foundation. The government has certain rights in the invention.

BACKGROUND OF THE INVENTION

5-Fluorouracil (5-FU) is well-established as a chemotherapeutic agent in the treatment of a variety of cancers (e.g. colon, pancreatic, breast). 5-FU irreversibly inhibits thymidylate synthase to block the synthesis of thymidine, an essential nucleotide required for DNA replication. 5-FU has been listed by the World Health Organization as one of the most important medications needed in a basic health system. However, there are many severe side effects associated with 5-FU treatment, including diarrhea, nausea, neutropenia, mouth sores, etc. Additionally, the resistance to 5-FU developed among patients also limits its clinical applications. Currently there is a need for new agents with a larger therapeutic window, lower toxicity, fewer side effects, increased solubility and/or improved pharmacokinetic profile that are useful for treating or preventing cancer.

Efficacy of active pharmaceutical ingredients (APIs) is known to be influenced by formulation methods. Among the formulation strategies being studied for solid form delivery of APIs, co-crystallization has been shown a promising means of improving physicochemical properties relative to effective drug delivery. Furthermore, a recent report on the use of a photodimer of 5-FU to function as a prodrug demonstrates the potential of delivering anticancer agents with excellent therapeutic efficacy to cancer cells, while avoiding side effects in normal cells (Q. Jin, F. Mitschang and S. Agarwal, *Biomacromolecules*, 2011, 12, 3684).

SUMMARY OF THE INVENTION

Accordingly the invention provides a compound of formula I:

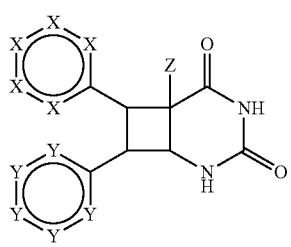

wherein:
each X is independently selected from the group consisting of —N=, —CH= and

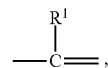

with the proviso that no more than two of X can be —N=;
each Y is independently selected from the group consisting of —N=, —CH= and

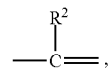

with the proviso that no more than two of Y can be —N=;
Z is halogen;
each $R^1$ and $R^2$ is independently selected from the group consisting of halo, hydroxy, $(C_1-C_4)$alkyl, $(C_2-C_4)$alkenyl, $(C_2-C_4)$alkynyl, $(C_1-C_4)$haloalkyl, $(C_1-C_4)$alkoxy, hydroxy $(C_1-C_4)$alkyl, —$NO_2$, —$N(R^a)_2$, —CN, —C(O)—N$(R^a)_2$, —O—$R^a$, —S—$R^a$, —O—C(O)—$R^a$, —C(O)—$R^a$, —C(O)—O$R^a$, —N$(R^a)$—C(O)—$R^a$ and —N$(R^a)$—C(O)—N$(R^a)_2$; and
each $R^a$ is independently hydrogen or $(C_1-C_4)$alkyl;
or a salt thereof.

The invention also provides a pharmaceutical composition comprising a compound of formula I or a pharmaceutically acceptable salt thereof, and a pharmaceutically acceptable carrier.

The invention also provides a method for treating or preventing cancer in an animal comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of cancer.

The invention also provides the use of a compound of formula I or a pharmaceutically acceptable salt thereof to prepare a medicament for treating cancer in an animal (e.g. a mammal such as a human).

The invention also provides processes and intermediates disclosed herein that are useful for preparing a compound of formula I or a salt thereof.

DETAILED DESCRIPTION

Figure 1:
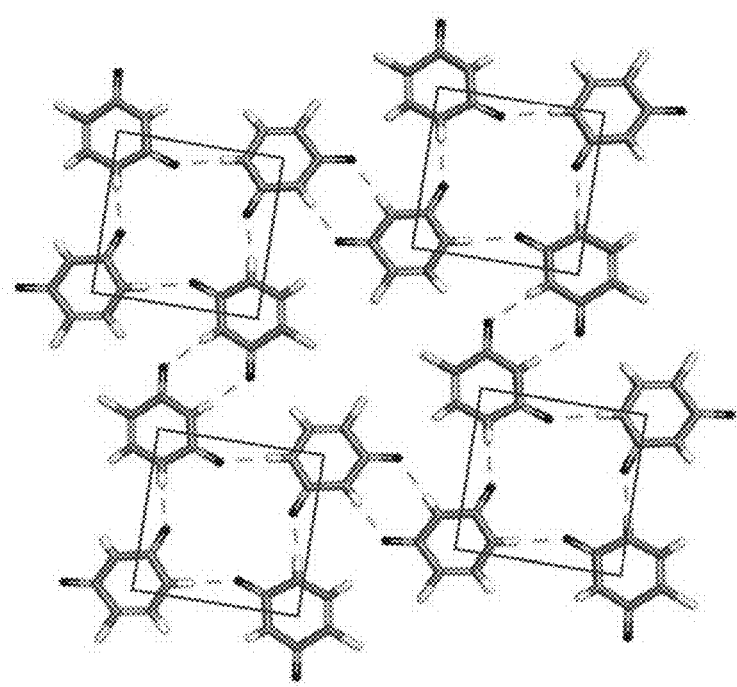
FIG. 1 shows crystal structure of 5-FU in Form I. 2-D network of 5-FU forms 4-pointed start motif.

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

Specifically, $(C_1-C_4)$alkyl can be methyl, ethyl, propyl, isopropyl, butyl, iso-butyl, sec-butyl; $(C_1-C_4)$alkoxy can be methoxy, ethoxy, propoxy, isopropoxy, butoxy, iso-butoxy, sec-butoxy; $(C_2-C_4)$alkenyl can be vinyl, allyl, 1-propenyl, 2-propenyl, 1-butenyl, 2-butenyl, 3-butenyl; $(C_2-C_4)$alkynyl can be ethynyl, 1-propynyl, 2-propynyl, 1-butynyl, 2-butynyl, 3-butynyl; halo$(C_1-C_4)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_4)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl.

The terms "treat" or "treatment" refer to therapeutic, prophylactic, palliative or preventative measures. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

The terms "cancer" and "cancerous" refer to or describe the physiological condition in animals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancers, including melanoma, as well as head and neck cancer.

The phrase "pharmaceutically acceptable" indicates that the substance or composition must be compatible chemically and/or toxicologically, with the other ingredients comprising a formulation, and/or the animal being treated therewith.

The phrase "pharmaceutically acceptable salt," as used herein, refers to pharmaceutically acceptable organic or inorganic salts of a compound of the invention.

The compounds of this invention also include other salts of such compounds which are not necessarily pharmaceutically acceptable salts, and which may be useful as intermediates for preparing and/or purifying compounds of this invention and/or for separating enantiomers of compounds of this invention.

The term "animal" means a warm-blooded animal that has or is at risk of developing a disease described herein and includes, but is not limited to, guinea pigs, dogs, cats, rats, mice, hamsters, and primates, including humans.

In one aspect the present invention provides for novel compounds of formula I:

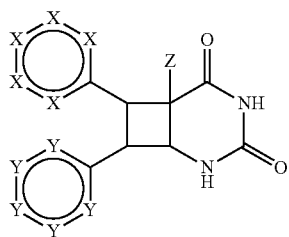

wherein:
each X is independently selected from the group consisting of —N═, —CH═ and

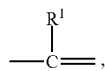

with the proviso that no more than two of X can be —N═;
each Y is independently selected from the group consisting of —N═, —CH═ and

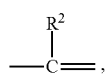

with the proviso that no more than two of Y can be —N═;
Z is halogen;
each $R^1$ and $R^2$ is independently selected from the group consisting of halo, hydroxy, ($C_1$-$C_4$)alkyl, ($C_2$-$C_4$)alkenyl, ($C_2$-$C_4$)alkynyl, ($C_1$-$C_4$)haloalkyl, ($C_1$-$C_4$)alkoxy, hydroxy ($C_1$-$C_4$)alkyl, —$NO_2$, —$N(R^a)_2$, —CN, —C(O)—$N(R^a)_2$, —O—$R^a$, —S—$R^a$, —O—C(O)—$R^a$, —C(O)—$R^a$, —C(O)—$OR^a$, —$N(R^a)$—C(O)—$R^a$ and —$N(R^a)$—C(O)—$N(R^a)_2$; and
each $R^a$ is independently hydrogen or ($C_1$-$C_4$)alkyl;
or a salt thereof.

In certain embodiments, one X is —N═, and each other X is independently —CH═ or

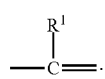

In certain embodiments, one Y is —N═, and each other Y is independently —CH═ or

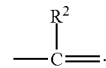

In certain embodiments, the compound of formula I has a structure of formula Ia:

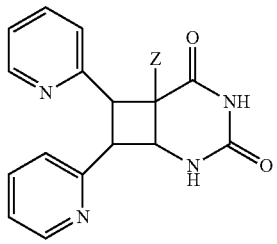

In certain embodiments, Z is —F.
In certain embodiments, the compound of formula I is:

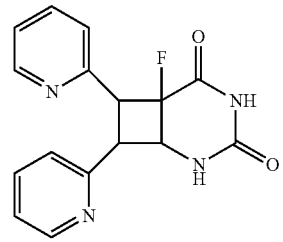 [SMILES: O=C1NC(=O)C2(F)C(N1)C(c1ccccn1)C2c1ccccn1]

or a salt thereof.

Processes for preparing compounds of formula I are provided as further embodiments of the invention and are illustrated by the following procedures, illustrated in Scheme 1, in which the meanings of the generic radicals (X, Y, Z) are as given above unless otherwise qualified.

Scheme 1

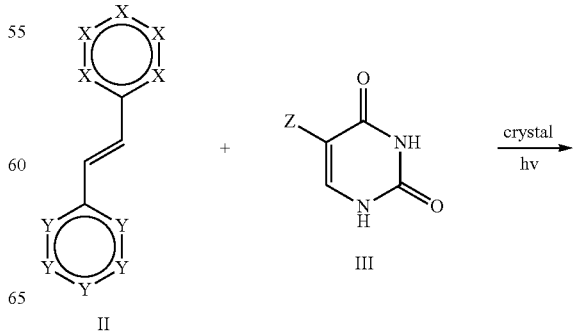

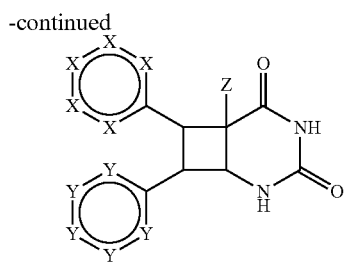

A compound of formula I can be prepared by reacting a corresponding compound of formula II with a corresponding compound of formula III in a solid state. The solid state is a two-component cocrystal comprising a compound of formula II and a compound of formula III. The cocrystals typically comprise a compound of formula II and a compound of formula III in a ratio of about 1 to 2. The process further comprises preparing the two component cocrystal by co-crystallizing the corresponding compounds of formula II and formula III. The process further comprises initiating a [2+2] photodimerisation reaction by light to provide the compound of formula (I).

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The suitable acid to react with basic compound can be selected from the group consisting of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (L), salicylic acid, sebacic acid, stearic acid, succinic acid, sulfuric acid, tartaric acid (+L), thiocyanic acid, toluenesulfonic acid (p) and undecylenic acid.

The compounds of formula I can be formulated as pharmaceutical compositions and administered to an animal host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable carrier such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The ability of a compound of the invention to treat cancer of an animal may be determined using pharmacological models or assays which are well known to the art.

The invention will now be illustrated by the following non-limiting Examples.

Example 1. Crystallization of 5-FU

Figure 2A:
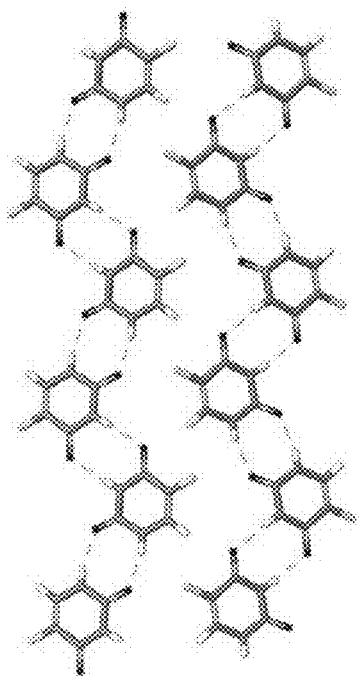
FIGS. 2a and 2b show crystal structure of 5-FU in Form II, top (FIG. 2a) and planar (FIG. 2b) views. 5-FU forms infinite 1-D chains that stack in slight zig-zag layers through offset, face-to-face π-π stacking.
Figure 2B:
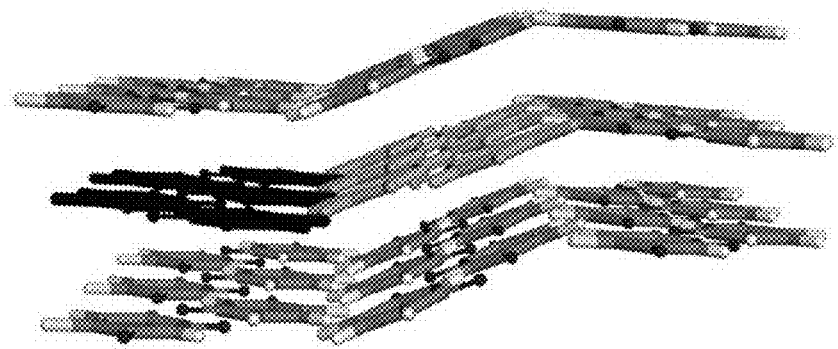

5-FU, in its pure form, exists in two known polymorphs. Form I is well known to crystallize from strongly polar solvents, being sustained by a network of N—H•••O hydrogen bonds accommodated by F-atoms (FIG. 1). The C=C bond separations in Form I lie beyond the distance of Schmidt (G. M. J. Schmidt, *Pure Appl. Chem.*, 1971, 27) for photoreaction. Form II was initially observed in a computational study and was predicted to be the lowest lattice energy structure before being obtained and characterized experimentally (A. T. Hulme, S. L. Price and D. A. Tocher, *J. Am. Chem. Soc.*, 2005, 127, 1116) (FIG. 2). The structure exhibits a ribbon motif wherein 5-FU engages in two separate amide dimers involving N—H•••O hydrogen bonds. The olefin separations between stacked ribbons are 3.79 and 3.91 Å, however the rings are canted at 26° relative to one another.

Example 2. Co-Crystallization of 5-FU and 2,2'-bipyridine (2,2'-bipy)

Figure 3A:
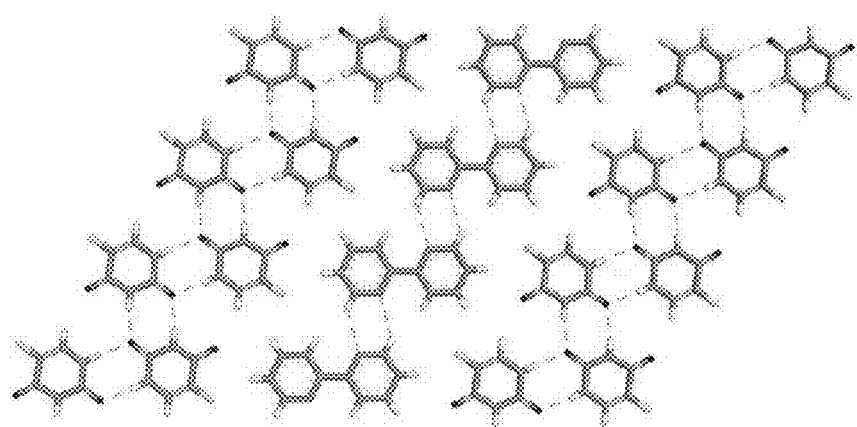
FIGS. 3a and 3b show cocrystal structure of 5-FU with 2,2'-bipyridine (2,2'-bipy), top (FIG. 3a) and planar (FIG. 3b) views. 5-FU forms infinite 1-D chains, similar to Form II. 5-FU chains are separated by infinite 1-D chains of 2,2'-bipy, formed through C—H⋯N interactions. Neighboring chains interact only through weak C—H⋯O and C—H⋯F forces.
Figure 3B:

Cocrystals of 2(5-FU)•(2,2'-bipy) were grown by slow evaporation from methanol solutions containing equimolar quantities of 5-FU and the respective bipyridine, providing single crystals suitable for X-ray diffraction studies after ca. 1 d (FIG. 3). The formulation of the corresponding cocrystals was further confirmed by 1H NMR spectroscopy.

The structure of 2(5-FU)•(2,2'-bipy) shows an interesting segregation between the two components whereby 1D ribbons of 5-FU pack in an alternating ABAB pattern with 1D ribbons of 2,2'-bipy. The asymmetric unit contains one 5-FU and one-half 2,2'-bipy. The 5-FU participates in a total of four N—H•••O hydrogen bonds, two bonds with each of two other 5-FU molecules. Though the molecular structure of 5-FU possesses two amide moieties, the structure shows that only one carbonyl oxygen participates as a hydrogen bond acceptor within the 5-FU ribbon. The motif is identical to the hydrogen-bonding patterns commonly observed in single component crystals of 5-FU analogues, but has never been observed as a polymorph of 5-FU itself (A. Delori, M. D. Eddleston and W. Jones, *Cryst Eng Comm*, 2013, 15, 73; A. T. Hulme, S. L. Price and D. A. Tocher, *J. Am. Chem. Soc.*, 2005, 127, 1116). The other carbonyl oxygen participates in a weak C—H•••O (carbonyl) interaction with a neighbouring 2,2'-bipy molecule. The X-ray data also suggest the hydrogen of the inter-ribbon C—H•••O (carbonyl) interaction may be bifurcated, its position hinting at the presence of a C—H•••F interaction between the same 5-FU and 2,2'-bipy (C•••F distance, C•••H•••F angle). The 2,2'-bipy ribbon is sustained by pairs of C—H•••N (pyridine) forces between neighboring 2,2'-bipy, each adopting an anti-conformation with respect to the nitrogen atoms. A view of the extended packing shows a noticeable offset between layers. Due to the close packing of the layers, the separation between olefins 5-FU in adjacent layers is still well within the limits set forth by Schmidt (3.76 Å). Single crystals were ground to a fine powder with a mortar and pestle and irradiated under a medium pressure Hg vapor lamp for 60 hours. No evidence of [2+2] cycloaddition is observed while monitoring the reaction by 1H NMR spectroscopy.

Example 3. Co-Crystallization of 5-FU and trans-(2-pyridyl)ethylene (2,2'-bpe)

Figure 4A:
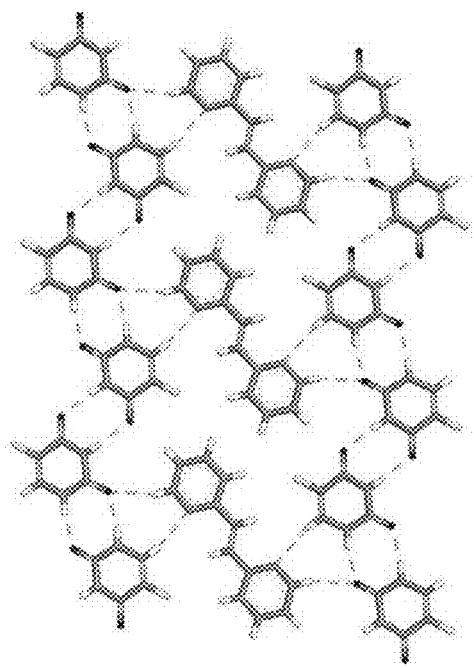
FIGS. 4a and 4b show cocrystal structure of 5-FU with trans-(2-pyridyl)ethylene (2,2'-bpe), top (FIG. 4a) and planar (FIG. 4b) views. 5-FU forms infinite 1-D chains, similar to Form II. The 2,2'-bpe intercalates between chains of 5-FU and is arranged by C—H⋯O and C—H⋯N interactions with 5-FU.
Figure 4B:
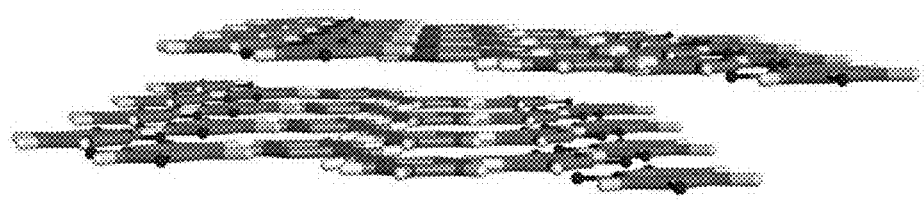

Cocrystals of 2(5-FU)•(2,2'-bpe) were grown by slow evaporation from methanol solutions containing equimolar quantities of 5-FU and the respective bipyridine, providing single crystals suitable for X-ray diffraction studies after ca. 1 d (FIG. 4). The formulation of the corresponding cocrystals was further confirmed by 1H NMR spectroscopy.

Figure 5A:
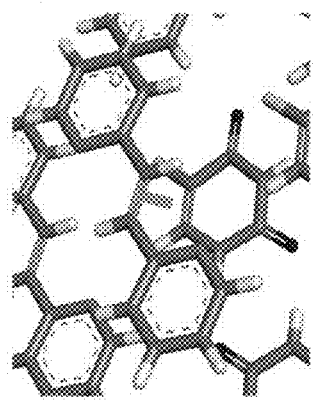
FIG. 5a shows expansion of X-ray crystal structure of nearest neighbor olefin separation in cocrystal of 5-FU with 2,2'-bpe.

Increasing the length of the bipyridine CCF has a significant effect on the behaviour of 5-FU. Primarily, 1D ribbons of 5-FU are present in the cocrystals of 2(5-FU)•(2,2'-bpe), however the nature of the hydrogen-bonding motif that forms them is markedly different. As opposed to cocrystals of 2(5-FU)•(2,2'-bipy) (Example 2), 5-FU in cocrystals of 2(5-FU)•(2,2'-bpe) fully realize the N—H•••O amide dimer synthon. Furthermore, both amide moieties are utilized in the elongation of the ribbon. The same motif dominates the structure of the rare Form II polymorph of 5-FU (A. T. Hulme, S. L. Price and D. A. Tocher, *J. Am. Chem. Soc.*, 2005, 127, 1116). In contrast to Example 2, the 5-FU ribbons in cocrystals of 2(5-FU)•(2,2'-bpe) are bridged by 2,2'-bpe. Adopting an anti-conformation, the 2,2'-bpe interacts with a total of four 5-FU molecules through both C—H•••O (carbonyl) and C—H•••N (pyridine) forces. There are, however, no noticeable interactions between adjacent 2,2'-bpe molecules. As in Example 2, the ribbons are arranged into planes that stack in an offset manner, producing a large degree of separation between olefins of 2,2'-bpe molecules in neighboring planes. The offset, however, is sufficient to bring the C=C bond of 2,2'-bpe close that of a 5-FU molecule in a neighboring layer at 3.44 Å and 3.57 Å separations although in a non-parallel alignment (FIG. 5a).

Example 4. [2+2] Photodimerisation of 5-FU and 2,2'-bpe

Figure 5B:
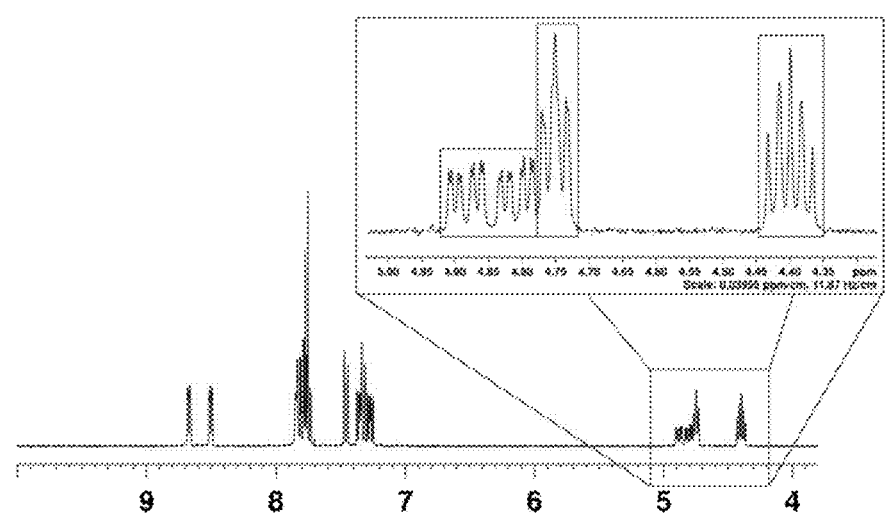
FIG. 5b shows $^1$H NMR spectrum of the dimerization occurring in 5-FU and 2,2'-bpe cocrystal.
Figure 6:
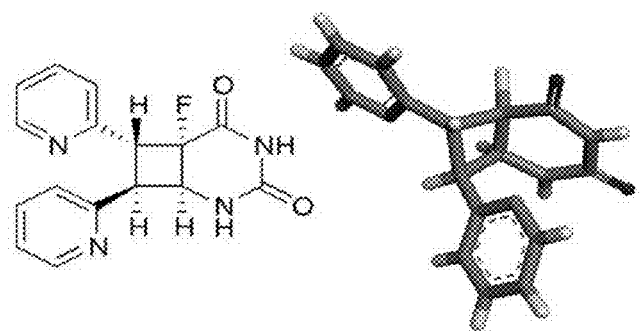
FIG. 6 shows single-crystal X-ray diffraction structure of compound 1.

Photoreactivity of the cocrystals of 2(5-FU)•(2,2'-bpe) was studied using the same approach, illustrated in Example 2, reaction progress again monitored by $^1$H NMR spectroscopy (FIG. 5b). After 35 h of irradiation, peaks at δ (ppm)=4.85, 4.75, and 4.40 support the formation of a cyclobutane ring with 98% conversion by relative integration. The irradiated powder was stirred in 1 M HCl until dissolved, the solution was made alkaline with $K_2CO_3$ and then extracted with dichloromethane (DCM). The organic layer was dried and the solvent removed under vacuum to provide the cross-photoproduct 1 as a white powder. The X-ray structure of 1 was obtained from single crystals grown by slow evaporation from isopropanol over the span of 1 day (FIG. 6). $^1$H NMR data is shown in FIG. 5b; HRMS (ESI+) calculated for $C_{16}H_{14}FN_4O_2$ [M+H$^+$] 313.1095, found 313.1114.

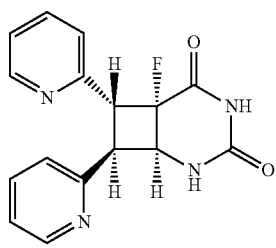

1

Example 5. Biological Evaluation

The effect of compound 1 on the viability and clonogenic survival on AR42J rat pancreatic tumor cells was examined by ATP viability assay and clonogenic survival assay. Results are presented compared to untreated controls.

ATP Based Viability Assay

Figure 7:
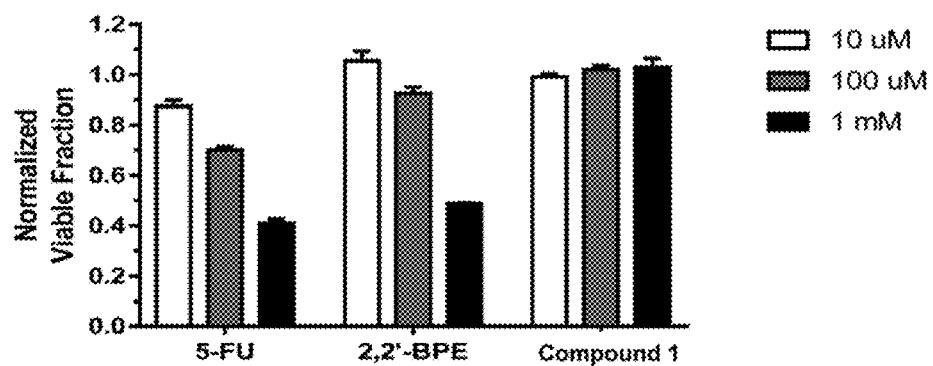
FIG. 7 shows normalized viable fraction of AR42J from 5-FU, 2,2'-Bpe, and compound 1 treatment of various concentrations. $5 \times 10^4$ cells were plated into a 96-well plate. After 48 h, the cells were treated with 10 µM, 100 µM, or 1 mM of 5-FU, 2,2'-Bpe, or compound 1 for 24 h. Relative intracellular ATP content were then measured using CellTiter-Glo Luminescent Cell Viability Assay (Promega). Data were normalized by untreated control and are represented as mean normalized viable fraction±S.D. (n=3). (see Example 5).

The cell viability assay was conducted using the CellTiter-Glo Luminescent Cell Viability Assay (Promega), which measures intracellular ATP present in metabolically active cells. AR42J rat exocrine pancreatic tumor cells were plated in a black, clear-bottom 96 multi-well plate at a density of $5.0\times10^4$ cells per well. After 48 h, the cells were treated with 10 μM, 100 μM, or 1 mM of 5-FU, 2,2'-bpe, or compound 1 for 24 h. The CellTiter-Glo reagent containing Luciferase and $Mg^{2+}$ was prepared as suggested by the product protocol and the equal volume (100 μL) of the reagent as the culture media was added to each well. The plate was then transfer to the SpectraMax microplate reader, mixed for 2 minutes for cell lysis, and the luminescence was recorded after 10 minutes. The results of the ATP based viability assay are shown in FIG. 7.

Clonogenic Survival Assay

Figure 8:
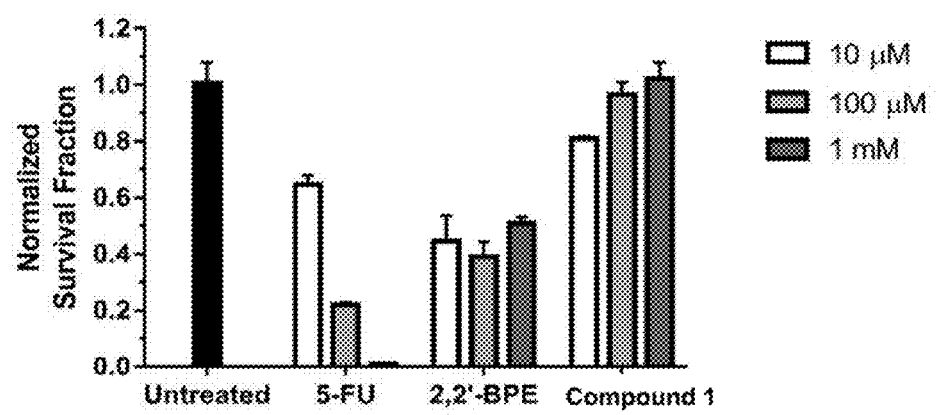
FIG. 8 shows normalized clonogenic surviving fraction of H727 from 5-FU, 2,2'-Bpe, and compound 1 treatment of various concentrations. $1.5 \times 10^4$ cells were plated into a 24-well plate, and after 4 days, the cells were treated with 10 µM, 100 µM, or 1 mM of 5-FU, 2,2'-Bpe, or compound 1 for 48 h. 1,500 cells were then re-plated to 6-well plates and the colonies were counted after 2 weeks of incubation. Data were normalized by untreated control and are represented as mean normalized survival fraction±S.D. (n==3).

NCI-H727 human bronchial carcinoid cells were plated in a 24-well plate at a density of $1.5\times10^4$ cells per well. After 4 days, the cells were treated with 10 μM, 100 μM, or 1 mM of 5-FU, 2,2'-bpe, or compound 1. Following 48 h treatment, the cells were washed once with ice cold PBS, collected, and re-plated to 6-well plates at a density of 1,500 cells per well. After 2 weeks of incubation, medium was aspirated and the colonies were fixed with 70% ethanol, followed by the Coommassie Brilliant Blue staining. Colonies were counted in the ImageJ software. The results of the clonogenic survival assay are shown in FIG. 8.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:
1. A compound of formula I:

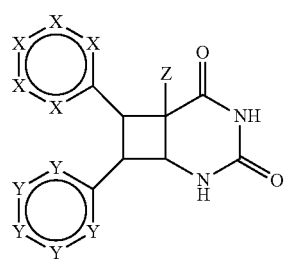

I or a salt thereof;
wherein each X is independently selected from the group consisting of —N=, —CH= and

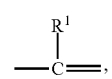

with the proviso that no more than two of X can be —N=;
each Y is independently selected from the group consisting of —N=, —CH= and

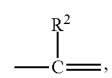

with the proviso that no more than two of Y can be —N=;
Z is halogen;
each $R^1$ and $R^2$ is independently selected from the group consisting of halo, hydroxy, ($C_1$-$C_4$)alkyl, ($C_2$-$C_4$)alkenyl, ($C_2$-$C_4$)alkynyl, ($C_1$-$C_4$)haloalkyl, ($C_1$-$C_4$)alkoxy, hydroxy($C_1$-$C_4$)alkyl, —$NO_2$, —$N(R^a)_2$, —CN, —C(O)—N(R$^a$)$_2$, —S—R$^a$, —O—C(O)—R$^a$, —C(O)—R$^a$, —C(O)—OR$^a$, —N(R$^a$)—C(O)—R$^a$ and —N(R$^a$)—C(O)—N(R$^a$)$_2$; and
each R$^a$ is independently hydrogen or (C$_1$-C$_4$)alkyl.

2. The compound of claim 1, wherein one X is —N═, and each other X is independently —CH═ or

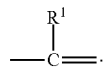

3. The compound of claim 1, wherein one Y is —N═, and each other Y is independently —CH═ or

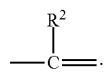

4. The compound of claim 1, which is a compound of formula Ia

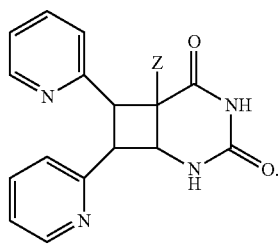

Ia

5. The compound of claim 1, wherein Z is —F.
6. The compound of claim 1, that is:

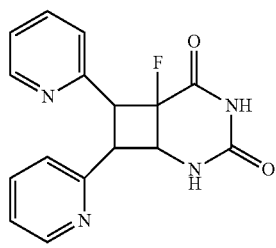 [SMILES: O=C1NC(=O)C2(F)C(N1)C(c1ccccn1)C2c1ccccn1]

or a salt thereof.

7. The compound of claim 1, that is in a salt form with an acid.

8. The compound of claim 7, wherein the acid is selected from the group consisting of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (L), salicylic acid, sebacic acid, stearic acid, succinic acid, sulfuric acid, tartaric acid (+L), thiocyanic acid, toluenesulfonic acid (p) and undecylenic acid.

9. A pharmaceutical composition comprising a compound as described in claim 1 or a pharmaceutically acceptable salt thereof, and a pharmaceutically acceptable carrier.

10. A method to prepare the compound of formula I as described in claim 1 comprising treating a solid state comprising a corresponding compound of formula II and a corresponding compound of formula III:

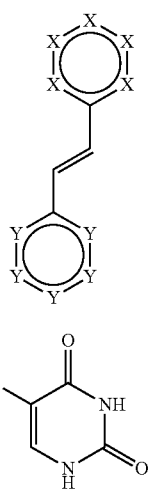

II

III wherein each X is independently selected from the group consisting of —N═, —CH═ and

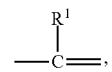

with the proviso that no more than two of X can be —N═;
each Y is independently selected from the group consisting of —N═, —CH═ and

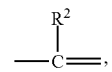

with the proviso that no more than two of Y can be —N═;
Z is halogen;
each R$^1$ and R$^2$ is independently selected from the group consisting of halo, hydroxy, (C$_1$-C$_4$)alkyl, (C$_1$-C$_4$)alkenyl, (C$_1$-C$_4$)haloalkyl, (C$_1$-C$_4$)alkoxy, —NO$_2$, —N(R$^a$)$_2$, —CN, —C(O)—N(R$^a$)$_2$, —O—R$^a$, —S—R$^a$, —O—C(O)—R$^a$, —C(O)—R$^a$, —C(O)—R$^a$, —N(R$^a$)—C(O)—R$^a$ and —N(R$^a$)—C(O)—N(R$^a$)$_2$;
each R$^a$ is independently hydrogen or (C$_1$-C$_4$)alkyl;
or a salt thereof
to provide the compound of formula I.

11. The method of claim 10 wherein the treating is done by light to initiate a [2+2] photodimerisation reaction to provide the compound of formula (I).

12. The method of claim 10 further comprising preparing the solid state by cocrystallizing the corresponding compounds of formula II and formula III to form cocrystals.

13. The method of claim 12, wherein the cocrystals comprise the compound of formula II and the compound of formula III in a ratio of 1 to 2.

* * * * *

UNITED STATES PATENT AND TRADEMARK OFFICE
CERTIFICATE OF CORRECTION

PATENT NO. : 9,937,177 B2  Page 1 of 1
APPLICATION NO. : 15/482323
DATED : April 10, 2018
INVENTOR(S) : Leonard R. MacGillivray It is certified that error appears in the above-identified patent and that said Letters Patent is hereby corrected as shown below:

In the Claims

Column 13, Line 1, Claim 1, please delete "-C(O)-N($R^a$)$_2$, -S-$R^a$," and insert
-- -C(O)-N($R^a$)$_2$, -O-$R^a$, -S-$R^a$, --;

Column 14, Line 63, Claim 10, please delete "-C(O)-$R^a$, -C(O)-$R^a$," and insert
-- -C(O)-$R^a$, -C(O)-O$R^a$, -- therefor.

Signed and Sealed this
Fifth Day of June, 2018

Andrei Iancu
*Director of the United States Patent and Trademark Office*